United States Patent [19]

Veal et al.

[11] 4,362,880
[45] Dec. 7, 1982

[54] CHEMICAL PROCESS

[75] Inventors: Kenneth T. Veal, Effingham; Trevor J. Grinter, Fetcham, nr. Leatherhead both of England

[73] Assignee: Beecham Group Limited, England

[21] Appl. No.: 249,004

[22] Filed: Mar. 30, 1981

[30] Foreign Application Priority Data

Apr. 11, 1980 [GB] United Kingdom ............... 8012077

[51] Int. Cl.$^3$ ................. C07D 333/24; C07D 239/00; C07D 211/20; C07D 403/00
[52] U.S. Cl. ........................................ 549/79; 549/59; 549/60; 549/76; 549/305; 549/310; 548/127; 548/215; 548/253; 548/336; 546/248; 546/284; 544/333; 544/405
[58] Field of Search ...................... 549/79, 59, 60, 76, 549/305, 310; 548/127, 215, 253, 336; 546/248, 284; 544/333, 405

[56] References Cited

U.S. PATENT DOCUMENTS 4,252,976  2/1981  Guest et al. ......................... 549/79

Primary Examiner—Alan Siegel
Attorney, Agent, or Firm—Jacobs & Jacobs

[57] ABSTRACT

An improved process for the preparation of 3-substituted thiophenes. The thiophenes are useful for the preparation of penicillins and cephalosporins.

The process is for the preparation of a thiophene of formula (I):

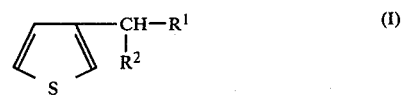

where $R^1$ represents a carboxylic acid group, or an ester or amide thereof or a nitrile group; $R^2$ represents a group suitable for use as an α-substituent in the side-chain of a penicillin or cephalosporin; which comprises treating under basic conditions a compound of formula (II):

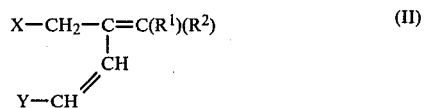

wherein X represents halogen or optionally functionalized hydroxyl, Y represents halogen, hydroxyl, or alkoxy; with a source of nucleophilic sulphur ionically bound to a polymeric support.

9 Claims, No Drawings

CHEMICAL PROCESS

This invention relates to a chemical process for the preparation of 3-substituted thiophenes, which are useful as intermediates in the production of penicillins and cephalosporins.

European Patent Application No. 783001407 (publication No. 0000633) discloses a process for the preparation of a thiophene of formula (I):

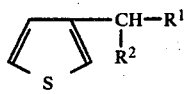

wherein $R^1$ represents a carboxylic acid group or an ester or amide derivative thereof or a nitrile (—CN) group; and $R^2$ represents hydrogen, a hydrocarbon or heterocyclic group, a carboxylic acid group or an ester or amide derivative thereof, or an acyl, nitrile, isonitrile (—NC) or optionally substituted imine group of formula —CH=NZ or —N=CHZ (where Z represents hydrogen, alkyl or aryl), or a sulphonyl, —$SR^a$, sulphoxide —$SO.R^a$ or sulphonate —$SO.OR^a$ group wherein $R^a$ represents $C_{1-6}$ alkyl, or aryl, which process comprises treating a compound of formula (II):

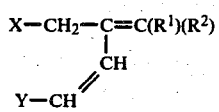

wherein $R^1$ and $R^2$ are as defined with respect to formula (I) above; X represents a halogen atom, a hydroxyl group or a functionalised hydroxyl group; and Y represents a halogen atom or a hydroxyl or alkoxy group; with a source of nucleophilic sulphur under basic conditions.

However, this process gives the desired thiophene often in poor yield and in an impure form. Subsequent purification of the product using vacuum distillation or chromatography frequently leads to further loss of product, and on a commercial scale substantially increases costs.

It has now been found that higher yields of compound (I) can be achieved by reacting the intermediate (II) with an insolubilised form of nucleophilic sulphur.

Accordingly the present invention provides a process for the preparation of a thiophene of formula (I) as defined hereinbefore which process comprises treatment of a compound of formula (II) as defined above under basic conditions with a source of nucleophilic sulphur ionically bound to a polymeric support which is insoluble in the reaction solution.

In formula (II) the group X should be readily displaced by nucleophilic attack. Such groups include chlorine, bromine, hydroxyl, arylsulphonyloxy such as benzenesulphonyloxy, p-toluenesulphonyloxy, or p-nitrosulphonyloxy, alkylsulphonyloxy such as methanesulphonyloxy or $C_{1-6}$ akanoyloxy such as acetoxy, propionoxy or butyroxy.

The group Y may be, for example, chlorine, bromine, hydroxy or $C_{1-6}$ alkoxy such as methoxy, ethoxy, or propoxy. Preferably both X and Y are halogen, especially chlorine.

Suitable sources of nucleophilic sulphur are for example the bisulphide ion, HS$^-$; the sulphide ion, S$^{2-}$; and the polysulphide ion. The source of nucleophilic sulphur is ionically bound to the polymeric support via charged groups present on the polymeric support.

Suitable polymeric supports may be derived from inorganic oxides such as silica, or organic polymers such as cellulose, dextrans such as Sephadex*, polyacrylamide, and cross linked polystyrene.

The charged groups on the polymeric support are suitably anionic groups such as for example the amino or quaternary ammonium group. Preferably the charged group is a quaternary ammonium group.

The polymeric support is preferably a basic ion-exchange resin, in particular a strongly basic ion-exchange resin based on cross-linked polystyrene. Specific anion exchange resins of this type include cross-linked polystyrene-divinyl benzene copolymers carrying a quaternary ammonium group, for example: Amberlite* IRA 904 which is a macroreticular strongly basic ion exchange resin with an exchange capacity when wet of 0.7 meq/ml, mesh size BSS 18-52, apparent water density 0.67 g/ml: and Amberlite* IRA 401 which is a high porosity basic ion exchange resin with an exchange capacity of 1.0 meq/ml when wet, 4.3 meq/ml when dry, mesh size BSS 14-52, apparent water density 0.69 g/ml.

*Amberlite and Sephadex are registered trademarks.

The cyclisation process may be carried out in a wide range of solvents subject to the solubility and reactivity of the reagents. Suitably the reaction is carried out in an inert organic solvent such as, for example, tetrahydrofuran, acetone, dimethylformamide, dimethylsulphoxide, hexamethylphosphoramide, acetonitrile, dimethoxyethane, dioxan, or an alcohol such as methanol, ethanol, propanol, butanol. Preferred solvents include tetrahydrofuran and acetone. An organic solvent such as methylene dichloride may also be employed, but is not a preferred solvent owing to the possibility of reaction with the nucleophilic sulphur.

The reaction may be carried out at ambient to elevated temperatures depending on the stability of the reagents used and the values of X, Y, $R^1$ and $R^2$. Preferably the temperature is in the range of 10° to 50° C.

Although it is possible to perform the cyclisation by stirring a solution of a compound of formula (II) with the polymeric support in a batch process, mechanical damage of the polymeric support may occur. It is preferable to pack the polymeric support into a column and pass a solution of a compound of formula (II) therethrough. Depending upon the speed of flow of the solution through the column and the reactivity of the reagents it may be preferable to pass the solution through the column a number of times to ensure a reasonable extent of reaction.

For convenience the polymeric support may be packed into a column in an alternative ionic form; for example, the commercially available anionic exchange resins are frequently supplied in either the hydroxide or chloride form. Exchange of the hydroxide or chloride ions for the source of nucleophilic sulphur is carried out using a conventional ion exchange process. Upon exhaustion of the source of nucleophilic sulphur the original ionic form of the polymeric support may be regenerated by a further ion exchange process.

Suitable bases which may be employed to provide the basic conditions for the process of this invention include inorganic bases, such as alkali metal hydroxides, preferably potassium hydroxide, and alkali metal bicarbonates preferably sodium bicarbonate and organic basis such as substituted amines for example tri($C_{1-6}$)alkylamines such as trimethylamine or triethylamine.

In some cases the polymeric support may be capable of providing the basic conditions necessary for the process of this invention; thus in a preferred embodiment of this invention the polymeric support is a basic ion-exchange resin.

The radicals $R^1$ and $R^2$ in compound (II) are chosen according to the requirements of the compound (I). For the preparation of penicillin and cephalosporin derivatives the group $R^1$ should be carboxylic acid group or a group which may be converted to a carboxylic acid group or a functional derivative thereof for acylation of the amino group of the penicillin or cephalosporin nucleus. The $R^2$ group is chosen to provide the required α-substituent, or a precursor thereof, for the side chain of a penicillin or cephalosporin.

The radical $R^1$ may be an ester group —$CO_2R^3$ wherein $R^3$ is an alkyl, cycloalkyl, alkenyl, alkynyl, aryl or heterocyclic group, any of which may be substituted. Suitable such $R^3$ groups include:

(a) alkyl especially $C_{1-6}$ alkyl such as methyl, ethyl, n- and iso-propyl, n-, sec-, and tert butyl, and pentyl;

(b) substituted $C_{1-6}$ alkyl wherein the substituent is at least one of: chloro, bromo, fluoro, nitro, carbo ($C_{1-6}$ alkoxy), $C_{1-6}$ alkanoyl, $C_{1-6}$ alkoxy, cyano, $C_{1-6}$ alkylmercapto, $C_{1-6}$ alkylsulfinyl, $C_{1-6}$ alkylsulphonyl, 1-indanyl, 2-indanyl, furyl, pyridyl, 4-imidazolyl, phthalimido, azetidino, aziridino, pyrrolidino, piperidino, morpholino, thiomorpholino, N-($C_{1-6}$ alkyl) piperazino, pyrrolo, imidazolo, 2-imidazolino, 2,5-dimethylpyrrolidino, 1,4,5,6-tetrahydropyrimidino, 4-methylpiperidino, 2,6-dimethylpiperidino, alkylamino, dialkylamino, alkanoylamino, N-alkylanilino, or substituted N-alkylanilino wherein the substituent is chloro, bromo, $C_{1-6}$ alkyl or $C_{1-6}$ alkoxy;

(c) cycloalkyl and ($C_{1-6}$ alkyl) substituted cycloalkyl having from 3 to 7 carbon atoms in the cycloalkyl moiety;

(e) alkynyl having up to 8 carbon atoms;

(f) phenyl and substituted phenyl wherein the substituent is at least one of chloro, bromo, fluoro, $C_{1-6}$ alkoxy, $C_{1-6}$ alkyl, $C_{1-6}$ alkanoyl, carbo-($C_{1-6}$) alkoxy, nitro, or di($C_{1-6}$) alkyl amino;

(g) benzyl or substituted benzyl wherein the substituent is chloro, bromo, fluoro, $C_{1-6}$ alkyl, $C_{1-6}$ alkoxy, $C_{1-6}$ alkanoyl, carbo($C_{1-6}$)-alkoxy, nitro, or di($C_{1-6}$-alkyl) amino;

(h) a 5- or 6-membered heterocyclic group containing one or more sulphur and/or nitrogen and/or oxygen atoms in the ring optionally fused to a second 5- or 6-membered hydrocarbyl or heterocyclic ring and which may be substituted with an alkyl group having 1 to 3 carbon atoms, for example thienyl, furyl quinolyl, methyl-substituted quinolyl, phenazinyl, pyridyl, methylpyridyl, phthalidyl, indanyl.

Preferred groups for $R^3$ include $C_{1-6}$ alkyl, benzyl, phthalidyl, indanyl, phenyl, mono-, di-, and tri- ($C_1$-$C_6$)alkyl substituted phenyl such as o-, m- or p-methylphenyl, ethylphenyl, n- or iso-propylphenyl, n-, sec-, iso- or butylphenyl.

Suitable groups $R^2$ include hydrogen, $C_{1-6}$alkyl, such as methyl, ethyl, propyl, or butyl, benzyl, phenyl, alkylphenyl, naphthyl, a 5- or 6-membered heterocyclic group containing one or more sulphur and/or nitrogen and/or oxygen atoms in the ring and which may be substituted by an alkyl group having from 1 to 3 carbon atoms, for example thienyl, imidazolyl, thiadiazolyl, isoxazolyl, methylisoxazolyl, tetrazolyl, methyltetrazolyl, pyrimidinyl, pyridyl, pyrazinyl, pyrrolidyl, piperidyl, morpholinyl, thiazinyl, furyl, or quinolyl; a carboxylic acid group, a carboxylic ester group —$CO_2R^3$ as defined above, or a $C_{1-6}$ alkanoyl group. When both groups $R^1$ and $R^2$ are ester radicals they may together form a cyclic ester group, for example isopropylidine of formula:

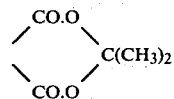

For the preparation of α-carboxy-3-thienyl penicillins and cephalosporins, $R^1$ and $R^2$ may conveniently both be carboxylic acid or ester radicals. It is convenient to prepare a diester compound of formula (I), i.e. where $R^1$ and $R^2$ both represent a group —$CO_2R^3$, and then halfsaponify in order to produce the compound (I) wherein one of $R^1$ and $R^2$ is a carboxylic acid group, suitable for coupling to the penicillin or cephalosporin nucleus.

Similarly for the preparation of an α-ester of an α-carboxy-3-thienyl penicillin or cephalosporin, the group $R^3$ may be chosen according to the eventual penicillin or cephalosporin required.

The compounds of formula (I) in which one of the groups $R^1$ and $R^2$ represents a carboxylic acid function may be converted to a penicillin or cephalosporin by a method known per se, for example as described in British Patent Specification Nos. 1,004,670, 1,125,557, 1,133,886, 1,193,302, W. German OLS No. 2,600,866.

Suitable procedures for the preparation of compounds of formula (II) are disclosed in European Patent Application No. 78300140.7 (Publication No. 0000633).

The following examples illustrate this invention.

EXAMPLE 1

3-Thienyl malonic acid

(a) (E)-1,4-Dichloro-3-buten-2-one

Ethyne (flow-rate 0.67 $dm^3$ $min^{-1}$) was passed through a propanone-cardice trap, an alumina drying tower and into a stirred suspension of aluminium chloride (0.715 kg, 5.36 moles) in dichloromethane (3 $dm^3$) while chlorethanoyl chloride (0.4 $dm^3$, 5.00 moles) was added portionwise over 20 minutes. On completion of the chloroethanoyl chloride addition, ethyne (5.36 moles, flow-rate as above) was passed into the solution for 3 hours. The dark brown solution was cooled and ice-water (1.8 $dm^3$) added slowly over 45 minutes. After separation the aqueous phase was extracted with dichloromethane (2×1 $dm^3$) and the combined extract washed with brine (2×1 $dm^3$), saturated sodium hydrogen carbonate solution (1 $dm^3$) and dried over magnesium sulphate (0.5 kg). Filtration and evaporation of the filtrate under reduced pressure gave the crude product as a dark brown oil 0.65 kg (93.5%); ca 90% pure.

(b) (E)-Methyl-2-carbomethoxy-5-chloro-3-chloromethyl-2,4-pentadienoate

Titanium tetrachloride (0.1 $dm^3$, 0.9 mole) in carbon tetrachloride (0.1 $dm^3$) was added to stirred tetrahydrofuran (0.25 $dm^3$) at 0° over 5 minutes. To the yellow solution a premix of 1,4-dichloro-3-buten-2-one (0.0556 kg, 0.4 mole) and dimethyl malonate (0.0528 kg, 0.4 mole) in tetrahydrofuran (0.2 dm$^3$) was added dropwise over 10 minutes maintaining the temperature at 0°. A solution of pyridine (0.13 dm$^3$, 1.6 moles) in tetrahydrofuran (0.1 dm$^3$) was added to the above brown mixture dropwise over 30 minutes at 0° and the resultant mixture stirred at ambient temperature for three hours and then treated with water (1 dm$^3$). The mixture was separated, the aqueous phase re-extracted with dichloromethane (2×0.25 dm$^3$) and the combined organic extract washed with brine (2×0.1 dm$^3$) and then dried over magnesium sulphate (0.10 kg). Filtration and evaporation of the filtrate under reduced pressure gave a red oil which crystallised on standing. Yield 0.064 kg (63.3%), m.p. 56°.

(c) Dimethyl 3-thienylmalonate

A solution of sodium sulphide nonahydrate (0.48 kg, 2 moles) in de-ionised water (4 dm$^3$) was eluted down a glass column containing Amberlite IRA-904(Cl) resin (1 dm$^3$). The resin was washed with de-ionised water (to remove excess sodium sulphide) until the washings were neutral (4 dm$^3$), followed by propanone (4 dm$^3$). Vacuum was then applied to the base of the column to partially dry the resin.

A solution of (E)-methyl-2-carbomethoxy-5-chloro-3-chloromethyl-2,4-pentadienoate (0.0506 kg, 0.2 mole) in propanone (0.5 dm$^3$) was then continually pumped around the column for 2.5 hours at 0.1 dm$^3$ min$^{-1}$. After this time the solution was collected and the resin washed with fresh propanone (3×1 dm$^3$). The combined propanone solution was evaporated to give an orange oil, 0.0472 kg (110%), which was dissolved in ethyl ethanoate (0.7 dm$^3$) and washed with water (3×0.2 dm$^3$). The organic extract was treated with charcoal (ca. 0.005 kg), dried over magnesium sulphate (0.10 kg), filtered and the filtrate evaporated under reduced pressure to yield dimethyl 3-thienylmalonate as a pale orange oil 0.0394 kg (92%; purity, g.l.c., 87%).

(d) 3-Thienylmalonic acid

Dimethyl 3-thienylmalonate, unpurified from the above reaction, (0.0385 kg, 0.18 mole) was added dropwise over 10 minutes to a stirred solution of sodium hydroxide (0.0157 kg, 0.39 mole) in water (0.065 dm$^3$) maintaining the temperature between 10°–20°. The resulting solution was stirred at ambient temperature for 1 hour and the methanol (formed in the hydrolysis) distilled under reduced pressure (Büchi, to ≦50°). The concentrate was cooled to 10°, 4-methyl-2-pentanone (0.040 dm$^3$) added and the pH adjusted to 5.0 with concentrated hydrochloric acid. The mixture was separated, the aqueous phase acidified to pH 3.0 (conc. HCl) and the solution extracted with dichloromethane (2×0.02 dm$^3$). After separation the aqueous phase was acidified to pH 1.0 (conc. HCl) and the solution extracted with diethyl ether (2×0.05 dm$^3$). The ethereal extract was treated with charcoal and dried over magnesium sulphate (0.01 kg). Filtration and evaporation of the filtrate gave a pale yellow gum that on trituration with dichloromethane (0.03 dm$^3$) yielded 3-thienylmalonic acid as a white powder 0.025 kg (75%), m.p. 138°–139°.

Elemental analysis: C, 45.7; H, 3.1; S, 17.3%; $C_7H_6O_4S$ requires: C, 45.2; H, 3.2; S, 17.2%.

Equivalent weight—purity 97.6%.

$^1$H n.m.r. and infra-red spectroscopy were consistent with 3-thienylmalonic acid.

EXAMPLE 2

Diethyl 3-thienylmalonate (a) (E)-ethyl 2-carboethoxy-5-chloro-3-chloromethyl-2,4-pentadienoate 1,4-Dichloro-3-buten-2-one (0.0556 kg, 0.4 mole) and diethyl malonate (0.064 kg, 0.4 mole) were condensed under identical conditions to those described in Example 1(b) to give the title compound 0.0865 kg (77%; purity, g.l.c., 87.85%).

(b) Diethyl 3-thienylmalonate

A solution of sodium sulphide nonahydrate (0.096 kg, 0.4 mole) in de-ionised water (0.2 dm$^3$) was passed down a glass column containing Amberlite IRA-904(Cl) resin (0.2 dm$^3$). The resin was washed with de-ionised water (to remove excess sodium sulphide) until the washings were neutral (1 dm$^3$), followed by propanone (1 dm$^3$). Vacuum was then applied to the base of the column to partially dry the resin.

A solution of (E)-ethyl 2-carboethoxy-5-chloro-3-chloromethyl-2,4-pentadienoate (0.013 kg i.e. 0.04 mole allowing for purity) in propanone (0.2 dm$^3$) was continually cycled around the column for 1.5 hours at 0.05 dm$^3$ min$^{-1}$. After this time the reddish coloured solution was collected and the resin washed with fresh propanone (2×0.5 dm$^3$). The combined propanone solution was evaporated under reduced pressure to give an orange oil 0.011 kg 100%. The oil was dissolved in diethyl ether (0.1 dm$^3$) and washed with water (2×0.1 dm$^3$). After separation the ethereal solution was treated with charcoal, magnesium sulphate and evaporated under reduced pressure to give the title compound as a pale yellow oil 0.0085 kg (77%; purity, g.l.c., 76%; activity yield 67%).

After washing the resin with propanone it was treated with de-ionised water (1 dm$^3$), 2 M-hydrochloric acid (1 dm$^3$) and de-ionised water (2 dm$^3$) to regenerate the resin into the Cl-form. The resin was then treated with sodium sulphide solution, de-ionised water and propanone as described above.

A solution of (E)-ethyl 2-carboethoxy-5-chloro-3-chloromethyl-2,4-pentadienoate (0.04 mole) in propanone (0.20 dm$^3$) was continually passed over the resin for 1 hour at 0.05 dm$^3$min$^{-1}$ and after work-up (exactly as described above) 0.009 kg (82%; purity, g.l.c. 75%) of 3-TME was isolated.

The resin was again regenerated to the chloride-form and then the sulphide-form as previous and a third sample of the ethyl pentadiene diester cyclised to give (VIb) 0.009 kg (82%; purity, g.l.c., 70%).

A soluttion of (E)-ethyl 2-carboethoxy-5-chloro-3-chloromethyl-2,4-pentadienoate (0.04 mole) in propanone (0.20 dm) was eluted down an ion-exchange resin in the sulphide-form (0.20 dm) over 1.0 hour. A g.l.c. assay indicated that ca. 60% of (E)-ethyl 2-carboethoxy-5-chloro-3-chloromethyl-2,4-pentadienoate had cyclised. The eluate was re-eluted down the column over 1.0 hour and a second assay indicated ca. 75% conversion. To obtain complete cyclisation the eluate was passed continually down the column for one hour.

We claim:

1. A process for the preparation of a thiophene of formula (I):

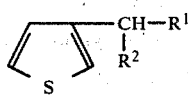

wherein $R^1$ represents a carboxylic acid group or an ester or amide derivative thereof or a nitrile group; and $R^2$ represents hydrogen, a hydrocarbon or heterocyclic group, a carboxylic acid group or an ester of amide derivative thereof; or an acyl, nitrile, isonitrile or optionally substituted imine group of formula —CH=NZ or —N=CHZ where Z represents hydrogen, alkyl or aryl, or a sulphonyl, —$SR^a$, sulphoxide —$SO.R^a$ or sulphonate —$SO.OR^a$ group wherein $R^a$ represents $C_{1-6}$ alkyl, or aryl, which process comprises treating a compound of formula (II):

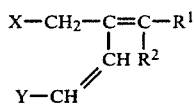

wherein $R^1$ and $R^2$ are as defined with respect to formula (I) above; X represents a halogen atom, a hydroxyl group or a functionalised hydroxyl group; Y represents a halogen atom, a hydroxyl group, or an alkoxy group; under basic conditions with a source of nucleophilic sulphur ionically bound to a polymeric support which is insoluble in the reaction solution.

2. A process as claimed in claim 1 wherein the polymeric support is a basic ion-exchange resin.

3. A process as claimed in claim 1, wherein the polymeric support is a strongly basic ion-exchange resin based on cross-linked polystyrene.

4. A process as claimed in claim 1, wherein the polymeric support is a cross-linked polystyrene-divinyl benzene copolymer carrying quaternary ammonium groups.

5. A process as claimed in claim 1, wherein X and Y are both halogen.

6. A process as claimed in claim 5 wherein X and Y are both chlorine.

7. A process as claimed in claim 1, wherein $R^2$ represents hydrogen, a carboxylic acid or ester group.

8. A process as claimed in claim 7 wherein $R^2$ is a carboxylic acid group or a carboxylic ester group of formula —$CO_2R^3$, wherein $R^3$ is $C_{1-6}$ alkyl, benzyl, phthalidyl, indanyl, phenyl, mono-, di-, or tri-($C_{1-6}$)-alkyl substituted phenyl.

9. A process as claimed in claim 1, wherein $R^1$ and $R^2$ both represent a carboxylic acid or ester group.

* * * * *